(12) United States Patent
Li et al.

(10) Patent No.: US 9,889,029 B2
(45) Date of Patent: Feb. 13, 2018

(54) IMPLANT DELIVERY SYSTEM

(71) Applicant: SHANGHAI MICROPORT MEDICAL (GROUP) CO., LTD., Shanghai (CN)

(72) Inventors: Yu Li, Shanghai (CN); Xiang Liu, Shanghai (CN); Mingming Wu, Shanghai (CN); Haishan Wang, Shanghai (CN); Guoming Chen, Shanghai (CN); Shaohui Chen, Shanghai (CN)

(73) Assignee: Shanghai Microport Cardioflow Medtech Co., Ltd., Shanghai (CN)

( * ) Notice: Subject to any disclaimer, the term of this patent is extended or adjusted under 35 U.S.C. 154(b) by 333 days.

(21) Appl. No.: 14/430,139

(22) PCT Filed: Sep. 22, 2013

(86) PCT No.: PCT/CN2013/083938
§ 371 (c)(1),
(2) Date: Mar. 20, 2015

(87) PCT Pub. No.: WO2014/044212
PCT Pub. Date: Mar. 27, 2014

(65) Prior Publication Data
US 2015/0223955 A1    Aug. 13, 2015

(30) Foreign Application Priority Data

Sep. 21, 2012  (CN) .......................... 2012 1 0356246

(51) Int. Cl.
*A61F 2/24*  (2006.01)
*A61F 2/962*  (2013.01)
(Continued)

(52) U.S. Cl.
CPC ............ *A61F 2/962* (2013.01); *A61F 2/2436* (2013.01); *A61F 2/82* (2013.01); *A61M 3/02* (2013.01);
(Continued)

(58) Field of Classification Search
CPC ........ A61F 2/2436; A61F 2/962; A61F 2/966; A61F 2002/9505; A61F 2002/9517
See application file for complete search history.

(56) References Cited

U.S. PATENT DOCUMENTS

2003/0144670 A1* 7/2003 Pavcnik ................ A61F 2/2436
606/108
2005/0027305 A1* 2/2005 Shiu .......................... A61F 2/95
606/108
(Continued)

FOREIGN PATENT DOCUMENTS

CN        2726560 Y      9/2005
CN    102196784 A1     9/2011
(Continued)

*Primary Examiner* — Ryan J Severson
*Assistant Examiner* — Christian Knauss
(74) *Attorney, Agent, or Firm* — Muncy, Geissler, Olds & Lowe, P.C.

(57) ABSTRACT

An implant delivery system is disclosed which includes an inner tube assembly, an outer tube assembly and a functional handle. The functional handle includes a threaded rod, a push-pull control member, a casing tube, a displacement tube, an inner tube fixing member, an outer tube fixing member and a stability tube fixing member. The threaded rod extends through a bore of the displacement tube. A fastener of the push-pull control member is able to engage a thread provided on a leading portion of the threaded rod. A trailing portion of the threaded rod is provided with a knob. The push-pull control member includes a fastener, springs and a button. The fastener is able to extend through a slot to engage a thread of the threaded rod in the displace- (Continued)

ment tube. The springs are configured to cause an automatic locking of the fastener and the threaded rod. The button is provided on the fastener. A cylindrical shell drives the displacement tube to move forward or backward along its longitudinal axis to cause the outer tube assembly to accordingly advance or retract. The delivery system can quickly, stably and accurately insert an implant into a target location.

18 Claims, 4 Drawing Sheets

(51) Int. Cl.
    *A61F 2/82* (2013.01)
    *A61M 3/02* (2006.01)
    *A61M 25/00* (2006.01)
    *A61M 25/01* (2006.01)
    *A61M 25/09* (2006.01)
    *A61M 39/10* (2006.01)
    *A61F 2/95* (2013.01)

(52) U.S. Cl.
    CPC .... *A61M 25/0021* (2013.01); *A61M 25/0074* (2013.01); *A61M 25/0108* (2013.01); *A61M 25/0136* (2013.01); *A61M 25/0147* (2013.01); *A61M 25/09* (2013.01); *A61M 39/10* (2013.01); *A61F 2002/9505* (2013.01); *A61F 2002/9517* (2013.01); *A61F 2250/0098* (2013.01); *A61M 2025/0177* (2013.01); *A61M 2205/0216* (2013.01)

(56) References Cited

U.S. PATENT DOCUMENTS

| 2007/0088431 | A1* | 4/2007 | Bourang | A61F 2/2433 623/2.11 |
|---|---|---|---|---|
| 2008/0188928 | A1* | 8/2008 | Salahieh | A61M 25/0054 623/2.11 |
| 2011/0251683 | A1* | 10/2011 | Tabor | A61F 2/2436 623/2.11 |

FOREIGN PATENT DOCUMENTS

| CN | 102258402 A | 11/2011 |
|---|---|---|
| WO | WO 2011/102970 A1 | 8/2011 |
| WO | WO 2011/137531 A1 | 11/2011 |

\* cited by examiner

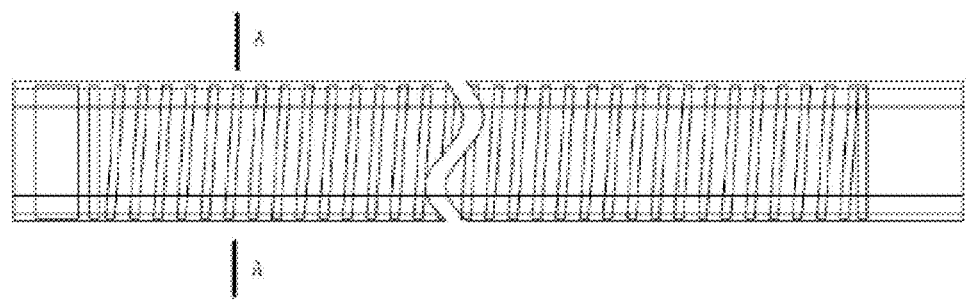
FIG. 6(a)
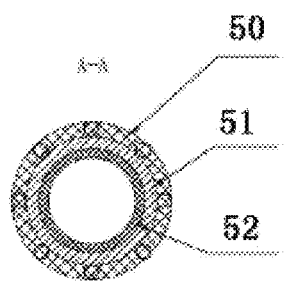
FIG. 6(b)
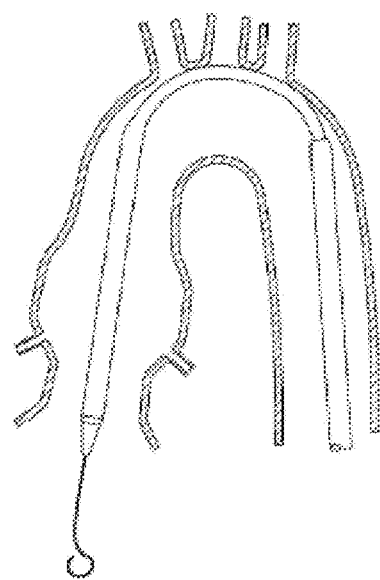

IMPLANT DELIVERY SYSTEM

TECHNICAL FIELD

The present disclosure relates to implant delivery systems and, more particularly, to systems for delivering and deploying a prosthetic heart aortic valve, mitral valve, tricuspid valve or pulmonic valve.

BACKGROUND

Heart valve diseases are some of most commonly diagnosed cardiac diseases in China, and most of them are found to be heart valve damage caused by rheumatic fever. In recent years, the continually aging population has driven an increasing incidence of valvular degeneration (including calcification, mucoid degeneration, etc.) and valvular damage caused by metabolic disorders.

Conventionally, heart valve replacement surgery is an open-heart procedure conducted under general anesthesia, during which, following an incision made along the patient's sternum (sternotomy), the heart is stopped and blood flow is guided through a "heart-lung" bypass machine (extracorporeal circulation machine). Traditional open surgery brings to the patient significant trauma as well as possible transient disturbances caused by emboli and other issues associated with the use of the heart-lung machine. Complete recovery from the trauma typically costs a couple of months. For some special population groups such as elders, the trauma is particularly unendurable and the recovery needs more time and is sometime even impossible.

Minimally invasive interventional surgery offers a variety of advantages, including needlessness of sternotomy, minimal patient trauma and quick recovery. In the recent ten years, interventional therapies have shown a tendency to be able to cope with not only all diseases curable by traditional medical and surgical treatments but also some diseases that the traditional approaches could not handle. Upon entering the new century, researches on interventional therapies for valvular heart diseases have been experiencing a notable acceleration. Percutaneous valve replacement technologies have evolved from experimental researches to small-scale clinical trials and are likely to have breakthroughs in technical "bottlenecks" to achieve extensive clinical applications. This makes the technologies again a focus of research efforts in the field of interventional cardiology.

Existing systems for delivering cardiac replacement valves are associated with a number of deficiencies. One of the deficiencies is that such systems are typically of high complexity which imposes great requirements on the clinician' operations and thus causes a high risk of operational mistakes. Another deficiency is that the existing delivery systems are incapable of rapid deployment and retrieve of delivering means after the replacement valve has been corrected located. This leads to an elongated time of their stay within the patient's body and hence increased adverse effects.

Chinese patent document (Patent No. CN2726560Y) describes a device for interventional implantation of a prosthetic heart valve. The device includes a delivery pipe, a locking silk, a pull line, a guide line, a pull line fixing bolt and a locking silk fixing bolt. The rear end of the delivery pipe is provided with at least one pull line branch pipe, each pull line enters the delivery pipe through each pull line branch pipe and extends out from the anterior end of the delivery pipe; each guide silk and each locking silk penetrates the delivery pipe and extends out from the anterior end of the delivery pipe; the pull line fixing bolt can be screwed at the pipe mouth of the pull line branch pipe to fix the pull line, the locking silk fixing bolt can be screwed at the rear end of the delivery pipe to fix the locking silk. While this device can achieve relatively satisfactorily controlled loading and deployment of the replacement prosthetic heart valve, it fails to address the high complexity issue as its operation involves manipulating the pull line and locking silk). Such complicated operation is more likely to cause mistakes and is detrimental to surgery time and quality.

US patent document (Pub. No. US2011/0251683A1) discloses a delivery system which reduces the requirements for the operating clinician and accordingly entails a reduced surgery time. However, in this system, the deployment of the replacement value is done by a significantly inconvenient rotating operation with an allowed angle of each rotation limited to lower than 180 degrees. While this deployment approach is less problematic during the location of the replacement valve, in the rapid deployment phase, it requires the clinician to rotate the control knob at a very high speed, thus leading to increased operational complexity. In addition, the system also suffers from unreliability in its "pushing-pulling" operation since the means for enabling this operation is prone to cause the clinician's finger to slip off during the operation. Finger slippery may lead to an overall movement of the delivery tubular structure which may, in turn, cause dislodgement of the deployed valve stent and thus undesirable conditions such as leakage. Other disadvantages of this conventional system include: inconvenient rotating operation of the functional handle; high risk of operational mistakes of the push-pull button; a single-layered construction of the inner tube assembly that is lack of balance between bending and axial performance.

In summary, the conventional systems have the deficiencies or drawbacks as follows:

1) high complexity that imposes great requirements on the clinician's operations and causes a high risk of operational mistakes;

2) a low operation efficiency because the coupling of the inner tube to a mounting frame provided on a trailing portion of the handle creates inconvenience in operating the rotating means and limits the stroke of each rotation to lower than 180 degrees;

3) incapability of satisfactory rapid deployment after correct location of the replacement valve, either by a pushing-pulling operation because this operation is unreliable as the button can be moved forward or backward only when it is in a pressed-down position, i.e., when being simultaneously driven by two forces from differing directions, which is prone to cause finger slippery and thus dislodgement of the located prosthetic valve, or by a rotating operation because in which the clinician is required to perform the inconvenient and complicated rotation operation at a high speed; and 4) difficulty in valve stent deployment when there occurs a relative rotation between the stent and the tubular structure because the rotation is prone to cause a shear force between a frame of the stent and retention clasps, which will impede the stent from being deployed.

Because of the above described shortcomings of the conventional delivery system, there exists a need for a novel delivery system can be controlled to deliver rapidly, reliably and precisely implantation of the prosthetic heart valve to an expected deployment location by uncomplicated minimally invasive operations.

SUMMARY OF THE INVENTION

In order to overcome the above described shortcomings of the conventional systems, the objective of the present disclosure is to provide implant delivery systems which enable rapidly, reliably and precisely interventional implantation of an implant to a target location by uncomplicated minimally invasive operations.

According to the disclosure, there is provided an implant delivery system, which includes an inner tube assembly, an outer tube assembly and a functional handle. The inner tube assembly includes, from a proximal end to a distal end in the sequence set forth, a reinforcing tube, a proximal inner tube, a stent ear holder, a distal inner tube and a tip; the inner tube assembly is configured to allow a guide wire to extend therethrough; the outer tube assembly is disposed over the inner tube assembly and includes, from a proximal end to a distal end, a proximal outer tube and a stent capsule, the proximal outer tube is received within a stability tube; the functional handle is connected to both the inner tube assembly and the outer tube assembly and the functional handle includes a threaded rod, a push-pull control member, a casing tube, a displacement tube, an inner tube fixing member, an outer tube fixing member and a stability tube fixing member, the inner tube fixing member is in fixed connection with a proximal portion of the inner tube assembly; the outer tube fixing member is in fixed connection both with a proximal end of the outer tube assembly and with a distal end of the displacement tube, the stability tube fixing member is in fixed connection with a proximal end of the stability tube and fixed to a distal end of the casing tube; the displacement tube is received within the casing tube such that the displacement tube moves forward and backward in the casing tube only along an axis direction of the casing tube; the threaded rod extends through a bore of the displacement tube; the threaded rod defines a leading portion and a trailing portion, the trailing portion of the threaded rod is provided with a knob; the push-pull control member includes a fastener and a button, the button is provided on the fastener; the displacement tube defines a slot compatible with the fastener, and the fastener is able to extend through the slot to engage a thread of the threaded rod in the displacement tube; the push-pull control member further includes a cylindrical shell and springs, and the cylindrical shell is disposed over the casing tube such that the button is able to extend out of the cylindrical shell through an opening thereof; the fastener assumes an annular shape and is engageable with the thread provided on the leading portion of the threaded rod; and the springs are disposed between the fastener and the displacement tube and configured to cause an automatic locking of the fastener and the threaded rod.

According to the above described arrangement of the present disclosure, as the components within the inner tube assembly forms a fixed structure and the knob provided on the trailing portion of the threaded rod is rotatable freely without any restrictions, a user can rotate the knob more efficiently to drive the displacement tube to move forth or back along the axis direction of the casing tube, thereby making the outer tube assembly advance or retract accordingly. This eliminates the need for use of the conventional mounting frame on the trailing portion, thereby allowing the rotating operation to be conducted freely at the trailing portion without any restrictions. Therefore, the implant delivery system of the present disclosure enables a convenient and efficient rotating operation. In operation of the functional handle of the implant delivery system, when the fastener is engaged with the thread of the threaded rod, by rotating the knob, the user can drive the displacement tube to move forward or backward along the axis direction of the casing tube to cause the outer tube assembly to accordingly advance or retract. In addition, the user can also manipulate the button to drive the fastener to move out of the engagement with the thread of the threaded rod and then push ahead or pull back the cylindrical shell to similarly drive the displacement tube to move forward or backward along the axis direction of the casing tube. As such, the rotating operation and the pushing-pulling operation are switchable at any time as desired. Further, in the implant delivery system of the present disclosure, the functional handle can achieve controlled deployment of an implant such as a valve stent at two different models, i.e., precisely deploy by rotating the knob and rapidly deploy by manipulating the button. Further, in operation of the implant delivery system, the user can further press the button downward with the same hand which is holding the cylindrical shell and performing the pushing-pulling operation. As such, the pressing operation and the pushing-pulling operation can be conducted either separately or concurrently to achieve easy, reliable and smooth delivering with less occurrence of finger slippery. Furthermore, the rotating and the pushing-pulling operations can be inter-switched arbitrarily at any position as desired. Thus, the implant delivery system is capable of rapid, reliable and precise interventional implantation of an implant to a target location without needing the clinician to do complicated operations.

Additionally, according to the present disclosure, as the fastener is annular and engaged with the thread of the threaded rod, it can be prevented from escaping from the thread due to a large longitudinal force generated during the deployment or retrieve of the implant such as, for example, a prosthetic heart valve. Further, the springs disposed between the fastener and the displacement tube are capable of not only effectuating the automatic locking of the fastener and the threaded rod but also providing convenience in removing their locking through manipulating the button. Moreover, loosening of the threaded engagement can be prevented by means of the connection of the thread of the threaded rod with the displacement tube via the fastener and the self-locking ability of the thread. Therefore, the engagement of the fastener and threaded rod allows an efficient rotating operation and thus enables the deployment and retrieve of the implant through rotating the knob.

Preferably, an auxiliary tube fits over a periphery of the proximal inner tube, and has a distal end abutting a proximal side of the stent ear holder and in fixed connection with both the stent ear holder and the proximal inner tube and a proximal end in connection with both the proximal inner tube and the reinforcing tube.

According to the above described arrangement of the present disclosure, the proximal inner tube and the auxiliary tube of the inner tube assembly forms a double-layered structure which can meet the requirements for both high axial strength and bending property, compared to a single-layered structure which generally exhibits a high tensile and compressive strength and hence a high force transfer ability but cannot meet the requirement for a high bending property due to a relatively large tube wall thickness. In the double-layered structure according to the present disclosure, the diametrically smaller proximal inner tube can be made of a metallic or polymeric material to obtain high tensile and compressive resistance capabilities, while its smaller diameter ensures a desirable bending property; and the auxiliary tube may be formed of a metallic or polymeric material in a helical construction such that it can provide protection for the proximal inner tube and prevent it from wobbling, and provide a good bending property at the same time.

Preferably, the tip is made of a flexible polymeric material and has a leading portion with a streamlined shape and a trailing portion with a straight shape. The trailing portion of the tip may have a straight shape portion with a beveled or rounded edge; and/or the tip is radiopaque.

According to the above described arrangement of the present disclosure, the streamlined shape of the tip formed of a flexible polymeric material can reduce the risk of body vascular damage occurring during its delivering, retrieve and retraction. In addition, the straight shape trailing portion of the tip can ensure a tight contact with the outer tube assembly during the retrieve of the prosthetic heart valve, thereby forming a smooth and stable contact between the outer tube assembly and the tip, which prevents the outer tube assembly from causing vascular damage. The beveled or rounded edge of the straight shape portion of the trailing portion of the tip allows the tip to nest in the outer tube assembly in a smooth manner prior to their contact. The traceability of the tip can be realized by embedding a radiopaque marker in the tip or adding a radiopaque material to the material of the tip. This provides the user with a visible indication which can facilitate the operation and location process.

Preferably, the distal inner tube is fabricated from a polymeric tube, a coil reinforced polymeric tube or a braid reinforced polymeric tube; and/or the distal inner tube has a stepped profile for loading an implant.

According to the above described arrangement of the present disclosure, the distal inner tube has a stepped profile, i.e., different outer diameters at different sections, for loading the implant. For example, the distal inner tube can have a smaller outer diameter at a section corresponding to a major portion of the implant such as, for example, a prosthetic heart valve, such that the implant can be crimped down to a minimal size. Additionally, the distal inner tube can have a greater outer diameter at a section corresponding to a proximal portion of the implant so as to form a tight contact with the implant, which is conducive to the delivering. The profile of the implant-loading portion of the distal inner tube that has differing diameters at different sections can ensure that the implant is partially crimped down to a minimal size and that, after the implant is loaded, a portion of it protruding out can well match the inner tube, thus resulting in an improvement in force transfer which in turn facilitates the deployment.

Preferably, the stent ear holder is made of a polymeric or metallic material and includes two or more clasps for connecting an implant, each of the clasps assuming a shape of a cylindrical boss; and/or the stent ear holder has end faces each defining an arc-shaped transition area; and/or the stent ear holder is radiopaque.

According to the above described arrangement of the present disclosure, the stent ear holder made of a metallic material or a highly radiopaque polymeric material can make the deployment process visible and thus facilitate the operation. Compared to clasps assuming a rectangular or other shape, the cylindrical boss-like clasps for connecting the implant such as a stent will generate less shear force with the frame of the stent and thus can ensure smooth disengagement of the implant. In other words, the cylindrical boss-like clasps can address the issue that the stent frame is difficult to be deployed due to a shear force formed with some other structure. In addition, the arc-shaped transition areas at the end faces of the stent ear holder can prevent the stent ear holder from scraping an inner surface of the outer tube assembly. Further, the traceability of the stent ear holder can facilitate observation of the deployment process during operation.

Preferably, the proximal inner tube is made of a polymeric or metallic material.

According to the above described arrangement of the present disclosure, fabricating the proximal inner tube that connects the stent ear holder and reinforcing tube at the two sides from a polymeric or metallic material with high axial tensile and compressive resistance can impart to the whole tubular structure both a high axial stability and a good bending flexibility.

Preferably, the auxiliary tube is formed of a polymeric material and the auxiliary tube is a polymeric catheter or defines a helical structure at a distal end. Preferably, the auxiliary tube is a metal spring.

According to the above described arrangement of the present disclosure, the auxiliary tube formed of a polymeric material or into a metal spring has high axial tensile and compressive resistance capabilities. In case of the auxiliary tube being made of a polymeric material, forming it to a polymeric catheter or forming a helical structure at its distal end can further impart to it high bending flexibility. The auxiliary tube is fitted over the periphery of the proximal inner tube such that a gap between them can be minimized and the inner tube will thus not bend or break under a pressure.

Preferably, the reinforcing tube is made of a polymeric or metallic material and has one end in connection with both the proximal inner tube and the auxiliary tube. In addition, the reinforcing tube is coupled to the functional handle via the inner tube fixing member, thereby securing the whole of the inner tube assembly to the functional handle.

Preferably, the outer tube assembly has a tapering shape, with the stent capsule having an outer diameter greater than that of the proximal outer tube; and/or both the stent capsule and proximal outer tube are fabricated from a polymeric tube and includes an outer layer, an intermediate layer and an inner layer, wherein the outer layer is formed of a high-strength polymeric material; the intermediate layer is a coil layer or a braid layer; and the inner layer is formed of a low-friction polymeric material.

According to the above described arrangement of the present disclosure, the structure of the outer tube assembly having diametrically different sections with different woven structure and different strengths can enable the different sections of the outer tube assembly to meet respective requirements for strength and bending flexibility.

Preferably, in case that the intermediate layer is a coil layer or a braid layer, axial stiffening ribs are evenly spaced about the periphery of the stent capsule.

According to the above described arrangement of the present disclosure, the stiffening ribs arranged on the coil layer or braid layer can result in an improvement in axial performance.

In addition, according to the present disclosure, the stent capsule is configured to load and retain the implant such as, for example, a prosthetic heart valve, and the proximal outer tube is connected to the functional handle via the outer tube fixing base. The stent capsule fabricated from a spirally- or braid reinforced polymeric tube has relatively high axial and radial performance. Moreover, the circumferentially distributed stiffening ribs on the coil reinforced or braid reinforced polymeric tube can result in a further improvement in its axial tensile and compressive resistance. A greater outer diameter of the stent capsule relative to the proximal outer tube ensures successful loading of the prosthetic heart valve.

Preferably, a section of the proximal outer tube adjacent to the stent capsule is fabricated from a coil reinforced or a pure tube and a section of the proximal outer tube remote from the stent capsule is fabricated from a braid reinforced tube; and/or the remote section of the stent capsule is provided with a radiopaque ring.

According to the above described arrangement of the present disclosure, the proximal outer tube can be divided into two sections in terms of functionality. The section adjacent to the stent capsule is fabricated from a coil reinforced or pure tube and can thus provide a high bending flexibility such that the tubular structure of the delivery system can easily pass through the aortic arch to reach the target implantation location without a significant counterforce from a section located between the aortic ventricle and the aortic arch, thereby facilitating the location and deployment to achieve a high deployment precision. Fabricating the section of the proximal outer tube remote from the stent retention outer from a braid reinforced tube can ensure a sufficient delivery force. High axial tensile and compressive resistance of the outer tube, as a whole, can make the deployment precision and retrieve free of influence from a possible movement of the outer tube. In addition, a gap between the outer tube and the auxiliary tube is minimized such that the inner tube will not bend or break under pressures. The inner layer of the outer tube can be formed of a low-friction material such as PTFE or provided with a coating layer which can reduce its friction coefficient, in order to facilitate the delivery of the outer tube. The radiopaque ring arranged on an end portion of the outer tube can facilitate the observation and location during the operation.

Preferably, the stability tube is fabricated from a coil or braid reinforced polymeric tube or a pure polymeric tube.

According to the present disclosure, the stability tube can be fabricated from a coil or braid reinforced or pure polymeric tube and contract to small openings at its free ends. The stability tube wholly encompasses the proximal outer tube so that the outer tube can move forth or back therein smoothly. In addition, the stability tube is fixedly connected to the functional handle and will not move with the deployment of the prosthetic heart valve.

Preferably, the inner tube fixing member is formed of a high-strength polymeric material or a metallic material, and the reinforcing tube of the inner tube assembly extends through a bore of the inner tube fixing member and is connected to the inner tube fixing member.

According to the above described arrangement of the present disclosure, the reinforcing tube can be firmly connected to the inner tube fixing member in the bore of which the reinforcing tube extends, using a fastener, an adhesive, a welding joint or the like.

Preferably, the outer tube fixing member includes an outer tube fixing base, an outer tube fixing screw cap, an outer tube sealing screw cap and an outer tube sealing ring. The proximal outer tube has an end portion expandable to a flare-shape and can thereby be connected to a distal portion of the outer tube fixing base. The distal portion of the outer tube fixing base has a conical structure matching in shape the flare-shaped end portion of the proximal outer tube. The outer tube fixing screw cap is fastened over the distal portion of the outer tube fixing base such that the flare-shaped end portion of the proximal outer tube is pressed on, and is thus in fixed connection with, the outer tube fixing base. The outer tube sealing screw cap is in connection with a proximal end of the outer tube fixing base. The outer tube sealing ring is disposed between the outer tube sealing screw cap and the proximal end of the outer tube fixing base and is configured to seal a lumen between the outer tube assembly and the inner tube assembly.

According to the above described arrangement of the present disclosure, a reliable, robust fastened connection with a high strength can be obtained at the expanded portion of the outer tube.

Preferably, the outer tube fixing base defines an aperture between the flare-shaped end portion of the proximal outer tube and the outer tube sealing ring, and the aperture is in connection with an outside of the implant delivery system via an outer tube flush port.

Preferably, the stability tube fixing member includes a stability tube fixing base, a stability tube fixing screw cap, a stability tube sealing screw cap and a stability tube sealing ring. The stability tube has an end portion expandable to a flare-shape and can thereby be connected to a distal portion of the stability tube fixing base. The distal portion of the stability tube fixing base has a conical structure matching in shape the flare-shaped end portion of the stability tube. The stability tube fixing screw cap is fastened over the distal portion of the stability tube fixing base such that the flare-shaped end portion of the stability tube is pressed on, and is thus in fixed connection with, the stability tube fixing base. The stability tube sealing screw cap is in connection with a proximal end of the stability tube fixing base. The stability tube sealing ring is disposed between the stability tube sealing screw cap and the proximal end of the stability tube fixing base and is configured to seal a lumen between the stability tube and the proximal outer tube.

According to the above described arrangement of the present disclosure, a reliable, robust fastened connection with a high strength can also be obtained at the expanded portion of the stability tube.

Preferably, the stability tube fixing base defines an aperture between the flare-shaped end portion of the stability tube and the stability tube sealing ring, and the aperture is in connection with an outside of the implant delivery system via a stability tube flush port.

Preferably, two limiting fins are provided on and distributed symmetrically along the displacement tube, and the casing tube defines two guide slots corresponding to the respective limiting fins. Each of the limiting fins has one end extending through the displacement tube and fixed to the inner tube fixing member and another end portion retained in a corresponding one of the guide slots of the casing tube.

Preferably, a Luer lock is in connection with the proximal portion of the inner tube assembly and thus with a lumen of the inner tube assembly.

According to the above described arrangement of the present disclosure, the Luer lock in connection with the proximal end of the inner tube assembly and thus with the lumen thereof can facilitate the emptying of a lumen of the delivery system as well as the passage of the guide wire.

According to the present disclosure, there is provided another implant delivery system, which includes an inner tube assembly, an outer tube assembly and a functional handle. The inner tube assembly includes, from a proximal end to a distal end in the sequence set forth, a reinforcing tube, a proximal inner tube, a stent ear holder, a distal inner tube and a tip; the inner tube assembly is configured to allow a guide wire to extend therethrough; the outer tube assembly is disposed over the inner tube assembly and includes, from a proximal end to a distal end, a proximal outer tube and a stent capsule, the proximal outer tube being received within a stability tube; the functional handle is connected to both the inner tube assembly and the outer tube assembly and includes a threaded rod, a push-pull control member, a casing tube, a displacement tube, an inner tube fixing member, an outer tube fixing member and a stability tube fixing member, the inner tube fixing member is in fixed connection with a proximal portion of the inner tube assembly, the outer tube fixing member is in fixed connection with a proximal end of the outer tube assembly and with a distal end of the displacement tube, the stability tube fixing member is in fixed connection with a proximal end of the stability tube and fixed to a distal end of the casing tube; the displacement tube is received within the casing tube such that the displacement tube moves forward and backward in the casing tube only along an axis direction of the casing tube; the threaded rod extends through a bore of the displacement tube; the threaded rod is fixed relative to the casing tube in the axis direction of the casing tube; and rotary relative to the casing tube in a circumferential direction of the casing tube; the threaded rod defines a leading portion and a trailing portion, the leading portion defining a thread, the trailing portion being provided with a knob; the push-pull control member includes a fastener and a button, the button is provided on the fastener; the displacement tube defines a slot compatible with the fastener, and the fastener is able to extend through the slot to engage the thread of the threaded rod in the displacement tube; and the threaded rod is provided, on its periphery, with a boss received in a recess formed in the casing tube, alternatively, the threaded rod defines, on its periphery, a recess accommodating a boss provided on the casing tube.

According to the above described arrangement of the present disclosure, the inner tube fixing member is disposed in and attached to the casing tube.

In summary, the implant delivery systems of the present disclosure can be operated more conveniently and accurately to achieve rapid, reliable and precise interventional implantation of an implant such as, for example, a prosthetic heart valve, to a target location without needing complicated operations of the clinician. In addition, in case of the implant not being deployed incorrectly, the implant delivery systems according to the disclosure can be operated to realize re-capture of the implant for an optional second location and deployment.

The above features and advantages of the present disclosure will be readily understood upon reading the following description of a few preferred embodiments shown in the accompany drawings.

BRIEF DESCRIPTION OF THE DRAWINGS

In order to further describe the principles of the present disclosure, a brief description of the accompanying drawings necessary to be referenced in the description of several specific embodiments of the disclosure is given below. Obviously, what are depicted in the accompanying drawings are merely several embodiments described in the present application, and those skilled in the art can make other drawings in light of these drawings without exerting creative efforts.

FIGS. 6(a) and 6(b) are diagrams showing a coil structure of the outer tube assembly of the implant delivery system according to the present disclosure, wherein FIG. 6(b) is a cross-sectional view taken along the line A-A in FIG. 6(a).

FIG. 7 is a schematic depicting a tube of a delivery device according to the present disclosure passing through an aortic arch.

FIG. 8 is an exploded and enlarged view of a functional handle according to the present disclosure, showing details of a displacement tube, a fastener and a cylindrical shell.

Figure 1:
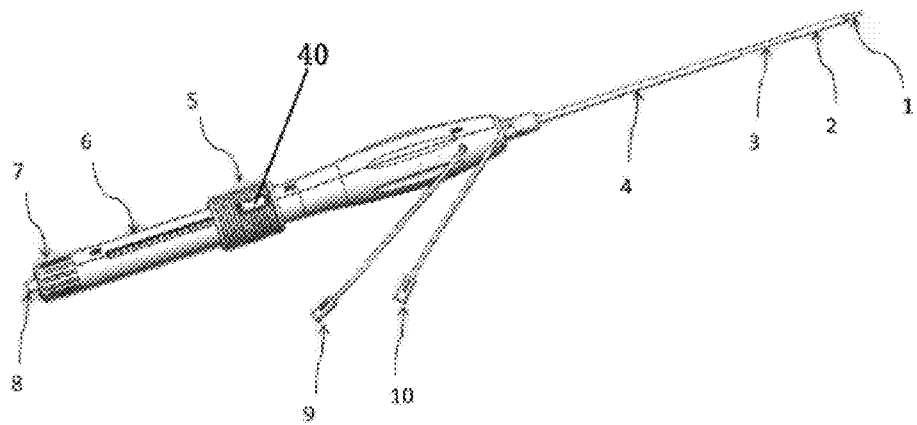
FIG. 1 is a schematic illustration of the overall configuration of a delivery system according to the present disclosure.

Reference numerals in the drawings are as follows:
1—tip; 2—stent capsule; 3—proximal outer tube; 4—stability tube; 5—cylindrical shell; 6—casing tube, 7—threaded rod, 8—Luer lock; 9—outer tube flush port; 10—stability tube flush port; 11—stability tube fixing screw cap; 12—stability tube fixing base; 13—stability tube sealing ring; 14—stability tube sealing screw cap; 15—outer tube fixing screw cap; 16—outer tube fixing base; 17—outer tube sealing ring; 18—outer tube sealing screw cap; 19—screw pins; 20—displacement tube; 21—inner tube fixing member; 22—fastener; 23—springs; 25—distal inner tube; 26—stent ear holder; 28—auxiliary tube; 29—reinforcing tube; 30—clasps; 31—aperture; 32—aperture; 33—recess; 34—boss; 35—protrusions; 36—protrusions; 38—proximal inner tube; 40—button; 41—knob; 50—outer layer; 51—intermediate layer; 52—inner layer.

DETAILED DESCRIPTION

Preferred embodiments of the present disclosure will be described in greater detail with reference to the accompanying drawings.

The description below references the accompanying drawings such that the principles of the embodiments will be thorough and fully understood. Obviously, the described embodiments are only part, rather than all, of the embodiments of the disclosure. All other embodiments made without exerting creative efforts by those skilled in the art in light of the embodiments disclosed herein are considered to be within the scope of the present disclosure.

The present disclosure discloses an implant delivery system. In particular, the disclosure discloses a system for delivering an interventional valve, which enables more convenient, reliable and rapid operations, including a rotating operation and a pushing-pulling operation, which are switchable at any time as desired, and has a tubular structure possessing excellent delivering and bending characteristics.

Figure 2:
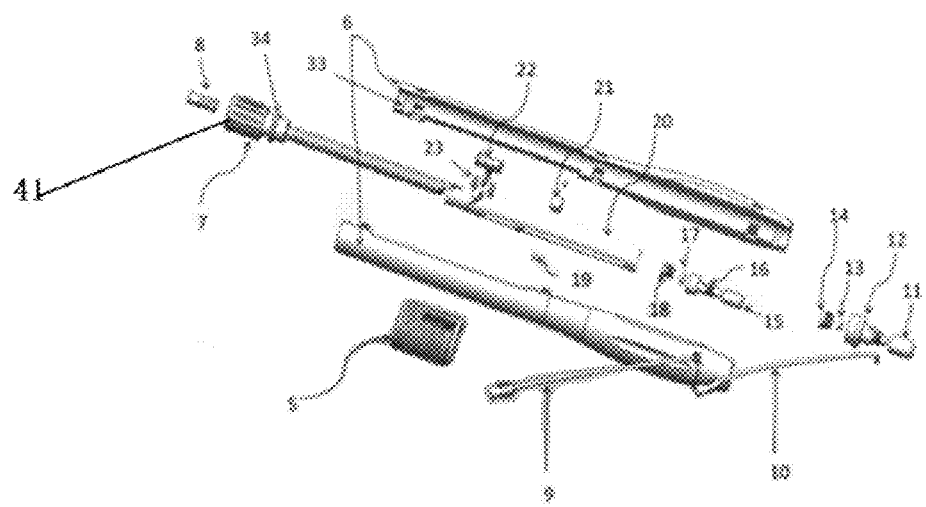
FIG. 2 shows an exploded view of a functional handle of the delivery system of FIG. 1.
Figure 3:
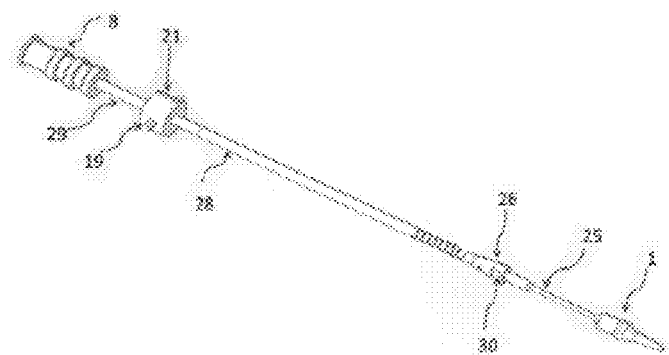
FIG. 3 schematically illustrates an inner tube assembly of the delivery system according to the present disclosure.
Figure 4:
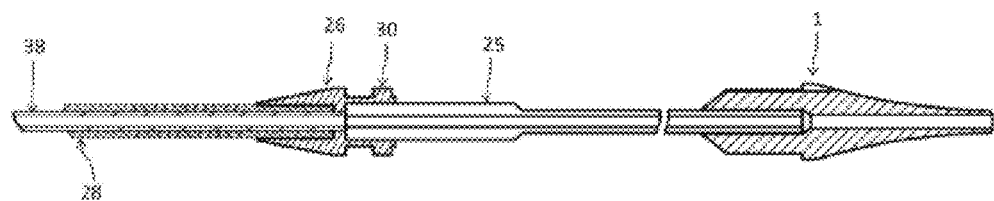
FIG. 4 is a longitudinal cutaway view taken along a longitudinal axis of the inner tube assembly of the delivery system according to the present disclosure.

Reference is first made to FIGS. 1 to 4, wherein FIG. 1 shows the overall configuration of a delivery system according to the present disclosure, FIG. 2 is an exploded view of a functional handle of the delivery system of FIG. 1, FIG. 3 schematically illustrates an inner tube assembly of the delivery system according to the present disclosure, and FIG. 4 is a longitudinal cross-sectional view taken along a longitudinal axis of the inner tube assembly of the delivery system according to the present disclosure.

As shown in FIG. 1, the implant delivery system according to the present disclosure generally includes a functional handle, an inner tube assembly and an outer tube assembly.

FIGS. 3 and 4 are a schematic of the inner tube assembly of the delivery system according to the present disclosure and a longitudinal cross-sectional view taken along a longitudinal axis of the inner tube assembly of the delivery system according to the present disclosure, respectively. The inner tube assembly includes, from a proximal end to a distal end, a reinforcing tube 29, a proximal inner tube 38, a stent ear holder 26, a distal inner tube 25 and a tip 1, coupled in series in this order. An auxiliary tube 28 fits over the periphery of the proximal inner tube 38, and a guide wire is able to extend through the inner tube assembly.

The tip 1 may be made of a flexible Pebax (polyether block amide) material, or of silicone or another flexible polymeric material, and the tip 1 is connected to the distal inner tube 25. The distal inner tube 25 may have a stepped profile and be fabricated from a braid reinforced Pebax tube, or from a coil reinforced tube or a pure polymeric tube. The stepped profile, i.e., a profile with different outer diameters at different sections, of the distal inner tube 25 is conducive to the loading of an implant. For example, the distal inner tube 25 may have a smaller outer diameter at a section corresponding to a major portion of the implant such as, for example, a prosthetic heart valve, such that the implant can be crimped down to a minimal size at this portion. In addition, the distal inner tube 25 may have a greater outer diameter at a section corresponding to a proximal portion of the implant, such that the distal inner tube can form a tight contact with a wall of the prosthetic heart valve, thereby allowing the valve to be delivered easily. Therefore, the profile of the implant-loading portion of the distal inner tube 25 that has differing diameters at different sections can ensure that the implant is partially crimped down to a minimal size and that, after the implant is loaded, a portion of the implant protruding out can well match the inner tube, thus resulting in an improvement in force transfer which in turn facilitates the deployment.

The distal inner tube 25 may be coupled to the stent ear holder 26. The stent ear holder 26 may be molded from a polymeric material added with a radiopaque material. Alternatively, the stent ear holder 26 may be formed by machining a polymeric or metallic material. Two clasps 30 may be provided symmetrically on the periphery of the stent ear holder 26. The clasps 30 may assume the shape of a cylindrical boss for retaining an implant such as a stent. However, the number of the clasps 30 may also be more. Each end portion of the stent ear holder 26 may define an arc-shaped transition area. In addition, the stent ear holder 26 may be implemented as a radiopaque component.

An auxiliary tube 28 may be fitted over the periphery of the proximal inner tube 38. The auxiliary tube 28 may be formed of a polymeric material or fabricated from a metal spring. The auxiliary tube 28 may be fixed at the both sides of the proximal inner tube 38. Specifically, the auxiliary tube 28 may be fitted over the periphery of the proximal inner tube 38, with a distal end of the auxiliary tube 28 abutting a proximal side of the stent ear holder 26 and in fixed connection with both the stent ear holder 26 and proximal inner tube 38, and with a proximal end of the auxiliary tube 28 connected to both the proximal inner tube 38 and the reinforcing tube 29. It is to be noted that in case of the auxiliary tube 28 formed of a polymeric material, a leading portion of the auxiliary tube 28 may be cut away and substituted by a helical structure. The proximal inner tube 38 may be fabricated from a thin-wall NiTi tube, or from a tube made of PEEK (polyetheretherketone) or other high-strength polymeric material, or from a metal tube. The reinforcing tube 29 (implemented as, for example, a stainless steel tube) is coupled to the inner tube fixing member 21 with screw pins 19, and the inner tube fixing member 21, in turn, secures the inner tube assembly, as a whole, to the casing tube 6 of the functional handle. The inner tube assembly may have a lumen with a uniform diameter so that the guide wire can pass therethrough in a smooth fashion.

Figure 5:
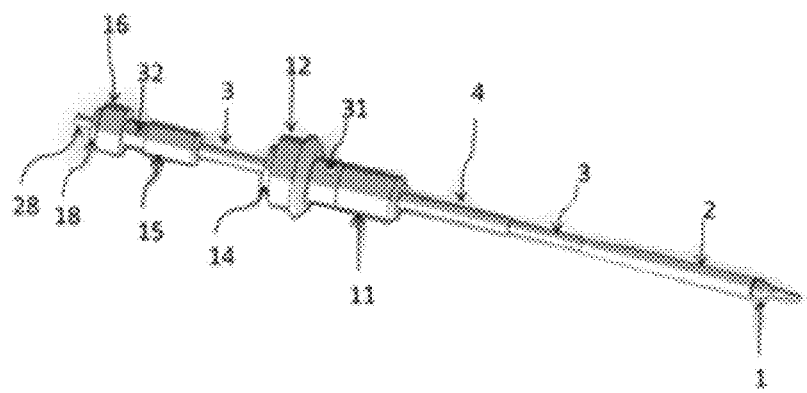
FIG. 5 shows an outer tube assembly of the delivery system according to the present disclosure.

FIG. 5 schematically depicts the outer tube assembly of the delivery system according to the present disclosure. The outer tube assembly is disposed over the inner tube assembly and includes, from a proximal end to a distal end, a proximal outer tube 3 and a stent capsule 2. The proximal outer tube 3 is received within a stability tube 4.

The stent capsule 2 may be fabricated from a polymeric tube and includes an outer layer formed of a high-strength polymeric material, an intermediate layer implemented as a coil layer and an inner layer formed of a low-friction polymeric material such as PTFE (polytetrafluoroethylene). Preferably, the polymeric tube has a diameter of 18 F (as used herein, F is a unit for measuring diameters of medical catheters, and 1 F≈0.33 mm). Alternatively, the intermediate layer may also be implemented as a braid layer. Further, the stent capsule 2 may be provided with axial stiffening ribs evenly arranged on its periphery.

Preferably, the proximal outer tube 3 has an outer diameter of 12 F. The proximal outer tube 3 can be generally divided into two sections, i.e., a proximal outer tube distal section and a proximal outer tube proximal section. The out layer of the proximal outer tube distal section adjacent to the stent capsule is made of a low-strength polymeric material, the intermediate layer is composed of coil wires and the inner layer is formed of a low-friction polymeric material such as PTFE. Alternatively, the proximal outer tube distal section adjacent to the stent capsule 2 is made from a high axial performance polymeric material. Further, the proximal outer tube proximal section may also be fabricated from a braid reinforced polymeric material and thus possesses high axial pushing-pulling performance.

The stent capsule 2 and the proximal outer tube 3 may be different parts of the same integral stepped tubular structure, or be interconnected by such an additional polymeric or metallic fastener that the resulting interconnected structure has a smooth shape and a continuous lumen.

The stability tube 4 may be fabricated from a braid reinforced polymeric tube and is disposed over the proximal outer tube 3 such that they can make smooth relative movements along the longitudinal direction.

FIGS. 6(a) and 6(b) show a coil structure of the outer tube assembly of the implant delivery system according to the present disclosure, wherein FIG. 6(b) is a cross-sectional view taken along the line A-A in FIG. 6(a). As shown in the figures, the stent capsule 2 and proximal outer tube 3 may each be fabricated from a polymeric tube and include: an outer layer 50, an intermediate layer 51 and an inner layer 52, in which, the outer layer 50 is made from a high-strength polymeric material, optionally provided with a reinforcing fiber layer; the intermediate layer 51 is a coil or a braid layer; and the inner layer 52 is formed of a low-friction polymeric material such as PTFE.

FIG. 2 depicts an exploded view of the functional handle of the implant delivery system of FIG. 1. As illustrated, the handle of the implant delivery system according to the present disclosure includes: a stability tube fixing screw cap 11, a stability tube fixing base 12, a stability tube sealing screw cap 14, a stability tube sealing ring 13, an outer tube fixing screw cap 15, an outer tube fixing base 16, an outer tube sealing screw cap 18, an outer tube sealing ring 17, a displacement tube 20, an inner tube fixing member 21, screw pins 19, a casing tube 6, an outer tube flush port 9, a stability tube flush port 10, a cylindrical shell 5, a fastener 22, springs 23 and a threaded rod 7.

The functional handle is in connection with both the inner and outer tube assemblies. Moreover, the functional handle specifically includes: a threaded rod 7, a push-pull control member, a casing tube 6, a displacement tube 20, an inner tube fixing member 21, an outer tube fixing member and a stability tube fixing member. The inner tube fixing member 21 is in fixed connection with a proximal portion of the inner tube assembly and is fixed to the casing tube 6. The outer tube fixing member is in fixed connection both with a proximal end of the outer tube assembly and with a distal end of the displacement tube 20. The stability tube fixing member is in fixed connection with a proximal end of the stability tube 4 and is secured to a distal end of the casing tube 6. The displacement tube 20 is received in the casing tube 6 and provided with limiting fins on its periphery such that it moves forward and backward in the casing tube 6 only along the axis direction of the casing tube. The threaded rod 7 extends through a bore of the displacement tube 20 and it is fixed relative to the casing tube 6 in the axis direction of the casing tube; and rotary relative to the casing tube 6 in a circumferential direction of the casing tube.

The threaded rod 7 defines a leading portion and a trailing portion. The leading portion defines a thread on its periphery and the trailing portion is provided with a knob 41. The push-pull control member includes a fastener 22, a cylindrical shell 5, springs 23 and a button 40. The fastener 22 is a cross-sectionally rectangular metal ring and thus the fastener 22 can engage the rectangular thread of the threaded rod 7. The springs 23 are disposed between the fastener 22 and the displacement tube 20 and are configured to cause an automatic locking of the fastener 22 and the threaded rod 7. The cylindrical shell 5 is disposed over the casing tube 6 such that the button 40 is able to extend out of the cylindrical shell 5 through an opening thereof. The displacement tube 20 defines a slot for the fastener 22 to pass therethrough to engage the thread of the threaded rod 7 that is disposed in the displacement tube 20. Once an engagement has been established between the fastener 22 and the threaded rod 7, the user is allowed to rotate the knob 41 to drive the displacement tube 20 to move forward or backward along the axis direction of the casing tube, and the movement of the displacement tube 20 will in turn drive the outer tube assembly to advance or retract accordingly. The user may also manipulate the button 40 to drive the fastener 22 to move out of the threaded engagement with the threaded rod 7 and then push or pull the cylindrical shell 5 to drive the displacement tube 20 to move forward or backward along the axis direction, thereby similarly achieving the advance or retraction of the outer tube assembly.

FIG. 8 is an exploded and enlarged view of the functional handle, showing details of the displacement tube 20, fastener 22 and cylindrical shell 5. Referring to FIGS. 2 and 8, the cylindrical shell 5 defines a rectangular opening and the button 40 can protrude out of the cylindrical shell 5 from the opening for the user's manipulation. The displacement tube 20 defines a slot compatible with the fastener 22 assuming the shape of an annular ring. The fastener 22 is able to pass through the slot and then engage the thread of the threaded rod 7 disposed in the displacement tube 20. Therefore, in the state of the fastener 22 being engaged with the threaded rod 7, the user can rotate the knob 41 to drive the threaded rod 7 to rotate synchronously. The rotation of the threaded rod 7 will drive the fastener 22 that is engaged with its thread to move forward or backward along the axis direction of the displacement tube 20. As the fastener is received in the slot of the displacement tube 20, the displacement tube 20 will move along the axis direction of the casing tube in the same way as the fastener 22. Since the distal end of the displacement tube 20 is connected to the outer tube fixing base 16 to which the outer tube assembly is secured, the outer tube assembly will accordingly move forward or backward along with the displacement tube 20. Therefore, when there is an engagement established between the fastener 22 and the thread of the threaded rod 7, the user can rotate the knob 41 to drive the displacement tube 20 to move forward or backward along the axis direction of the casing tube, thus making the outer tube assembly advance or retract accordingly.

Instead of the above-described rotating operation on the knob 41, the user may achieve the same purpose by performing a pushing-pulling operation on the functional handle. Specifically, the user can hold the cylindrical shell 5 and press the button 40 downward so as to lower the fastener 22 to a lower position, thereby removing the threaded engagement between the fastener 22 and the threaded rod 7. The displacement tube 20 forms on its periphery two protrusions 35 projecting in 180 degrees opposite directions, while the cylindrical shell 5 defines four protrusions 36, with each two of the protrusions 36 corresponding to one of the two protrusions 35. In a normal assembled position, each protrusion 35 is located between corresponding two of the protrusions 36. As can be understood by those skilled in the art, the present disclosure is not limited to the above described numbers and structures of the protrusions 35 and 36 because any number of the protrusions 35 and 36 with any structure are acceptable if they can effectuate the connection of the cylindrical shell 5 and the displacement tube 20. With the fastener 22 being pressed to the lower position, the user can push or pull the cylindrical shell 5 along the axis direction of the displacement tube 20 to cause the displacement tube 20 to accordingly advance or retract with the forward or backward movement of the cylindrical shell 5 because of their connection established by the protrusions 35 and 36. As the distal end of the displacement tube 20 is connected to the outer tube fixing base 16 to which the outer tube assembly is secured, the outer tube assembly will also move forward or backward along with the displacement tube 20. That is, the user can also achieve the advance and retraction of the outer tube assembly by manipulating the button 40 to drive the fastener 22 to move out of the threaded engagement between the fastener 22 and the threaded rod 7 and then moving the cylindrical shell 5 to drive the displacement tube 20 to move forward or backward in the same way along the axis direction of the casing tube.

As shown in FIGS. 2 and 5, the stability tube fixing member according to the present disclosure may include a stability tube fixing base 12, a stability tube fixing screw cap 11, a stability tube sealing screw cap 14 and a stability tube sealing ring 13. When there is a connection established between the stability tube 4 and the functional handle, an end portion of the stability tube 4 may be expanded to the shape of a flare and then disposed over the periphery of a corresponding connecting portion (namely distal portion) of the stability tube fixing base 12. The stability tube fixing screw cap 11 may then be further capped and screw-fastened over the stability tube fixing base 12. The connecting portion of the stability tube fixing base 12 may be a conical structure that matches in shape the flare-shaped end portion of the stability tube 4. The stability tube fixing screw cap 11 may be fastened over a distal portion of the stability tube fixing base 12 such that the flare-shaped end portion of the stability tube 4 is pressed and is thus in fixed connection with the stability tube fixing base 12. In addition, the stability tube sealing screw cap 14 may restrain the stability tube sealing ring 13 in a bore of the stability tube fixing base 12 such that after the proximal outer tube 3 is inserted in the bore of the stability tube fixing base 12, the stability tube sealing ring 13 tightly embraces the periphery of the proximal outer tube 3, thereby sealing a lumen between the outer tube and the stability tube. The casing tube 6 may consist of two parts which can be fastened together and thereby fix the stability tube fixing base 12.

The outer tube fixing member according to the present disclosure may include an outer tube fixing base 16, an outer tube fixing screw cap 15, an outer tube sealing screw cap 18 and an outer tube sealing ring 17. In a state of the proximal outer tube 3 being connected to the functional handle, an end portion of the proximal outer tube 3 may be expanded to the shape of a flare and then disposed over the periphery of a corresponding connecting portion (namely distal portion) of the outer tube fixing base 16. The outer tube fixing screw cap 15 may then be further capped and screw-fastened over the outer tube fixing base 16. The connecting portion of the outer tube fixing base 16 may be a conical structure that matches in shape the flare-shaped end portion of the proximal outer tube 3. The outer tube fixing screw cap 15 may be fastened over a distal portion of the outer tube fixing base 16 such that the flare-shaped end portion of the proximal outer tube 3 is pressed and is thus in fixed connection with the outer tube fixing base 16. The outer tube sealing screw cap 18 may restrain the outer tube sealing ring 17 in a bore of the outer tube fixing base 16 such that after the proximal inner tube 38 is inserted in the bore of the outer tube fixing base 16, the outer tube sealing ring 17 tightly embraces the periphery of the proximal inner tube 38, thereby sealing a lumen between the inner tube and the outer tube. The outer tube fixing base 16 may be in fixed connection with the displacement tube 20.

When the inner tube assembly is connected to the functional handle, an end portion of the reinforcing tube 29 of the inner tube assembly may extend successively through the stent capsule 2, the bore of the inner tube fixing member 21 and the bore of the threaded rod 7, and the trailing portion of the inner tube assembly is connected with a Luer lock 8. The inner tube assembly, as a whole, may connect the reinforcing tube 29 and the inner tube fixing member 21 with two symmetrically distributed screw pins 19. The inner tube fixing member 21 may be disposed in the bore of the displacement tube 20, and each of the fixing screw pins 19 may have a section projecting from the inner tube fixing member 21, which extends through a corresponding one of two guide slots formed symmetrically in the displacement tube 20 and is then fixed to the casing tube 6. As a result, limited by the fixing screw pins 19 and the guide slots, the displacement tube 20 only move in a direction of the guide slots. A trailing portion of the displacement tube 20 may define a slot having the same width as the annular fastener 22 and extending downward obliquely at an angle relative to the axis direction of the displacement tube 20 that is exactly equal to a lead angle of the thread of the threaded rod 7. Therefore, in a state of the fastener 22 being received in the oblique slot, when the threaded rod 7 is inserted in the bore of the displacement tube 20, the thread of the threaded rod 7 will be engaged with the annular fastener 22.

The displacement tube 20 may be provided on its periphery with two structurally symmetric limiting fins retained in respective two guide slots appearing in the casing tube 6 when the two parts of the casing tube 6 are fastened together such that the displacement tube 20 can only move forward or backward without rotation. Specifically, each of the limiting fins symmetrically distributed on the periphery of the displacement tube 20 may have one end that extending through the displacement tube 20 and fixed to the inner tube fixing member 21 and the other end restrained within a corresponding one of the two guide slots symmetrically formed in the casing tube 6. A button 40 may be provided on the fastener 22 and two springs 23 may be arranged beneath the button 40. In a default configuration, the springs 23 may be in a compressed state such that the fastener 22 is pushed to a topmost position, thereby enabling the threaded engagement of the annular portion of the fastener 22 with the threaded rod 7.

A trailing portion of the threaded rod 7 may define a boss 34 which can be engaged with a recess 33 appearing in a trailing portion of the casing tube 6 when the two parts of the casing tube 6 are fastened together such that the threaded rod 7 is restrained in the casing tube 6 and can only rotate therein circumferentially. Alternatively, the threaded rod 7 may define in its periphery a recess which is engageable with a boss formed on the casing tube 6.

The stability tube flush port 10 may have one end connected with the bore of the stability tube fixing base 12 and thus with a lumen between the stability tube 4 and the proximal outer tube 3. The stability tube fixing base 12 may define an aperture 31 situated between the portion of the stability tube 4 disposed over the stability tube fixing base 12 and the stability tube sealing ring 13 proximal to the trailing portion of the stability tube fixing base 12. The aperture 31 may be connected to the outside of the system via the stability tube flush port 10. The other end of the stability tube flush port 10 may be connected with a stop valve which can be used to empty the aforesaid lumen or self-locked to close the lumen.

The outer tube flush port 9 may have one end connected with the bore of the outer tube fixing base 16 and thus with a lumen between the proximal inner tube 38 and the proximal outer tube 3. The outer tube fixing base 16 may define an aperture 32 situated between the portion of the outer tube disposed over the outer tube fixing base 16 and the outer tube sealing ring 17 proximal to the trailing portion of the outer tube fixing base 16. The aperture 32 may be connected to the outside of the system via the outer tube flush port 9. The other end of the outer tube flush port 9 may be connected with a stop valve which can be used to empty the aforesaid lumen or self-locked to close the lumen.

In operation of the implant delivery system, by manipulating the knob 41 provided on the trailing portion of the threaded rod 7, the displacement tube 20 can be moved forward or backward to drive the outer tube to advance or retract. Alternatively, the user can also manipulate the button 40 of the fastener 22 to remove the threaded engagement between the fastener 22 and the threaded rod 7 and then push ahead or pull back the cylindrical shell 5 to drive the displacement tube 20 to move forward or backward, thereby similarly achieving the advance or retraction of the outer tube. Further, the above rotating operation and pushing-pulling operation are switchable arbitrarily. In addition, during the operation, as the stability tube 4 remains stationary with respect to the casing tube 6 of the functional handle and the advance or retraction of the outer tube occurs inside the stability tube 4, movement of the delivery device can be prevented to ensure a high deployment precision of the implant such as, for example, a prosthetic heart valve. Moreover, as the inner tube fixing member 21 keeps stationary relative to the functional handle, dislodgement of the deployed implant such as a prosthetic heart valve can also be avoided. When the tubular structure of the system enters the human body and is approaching the aortic arch, the streamline-shape flexible tip 1 and the portion of the proximal outer tube 3 adjacent to the stent capsule 2, as well as the high bending flexibility of the double-layered inner tube assembly, allow the tubular portion to smoothly pass through the aortic arch to deliver the prosthetic heart valve stent to the position of the defective heart valve. In addition, the high bending flexibility of the outer and inner tube assemblies enables a reduced reaction force from the tubular components during the location of the prosthetic heart valve. This can decrease the risk of dislodgement of the deployed prosthetic heart valve, thus assuring a high location and deployment precision. Further, safety of the surgery can be ensured by removing air in the lumens of the inner, outer and stability tubes using the Luer lock 8, the outer tube flush port 9 and the stability tube flush port 10. FIG. 7 is a schematic depicting a tube of a delivery device using the implant delivery system according to the present disclosure passing through an aortic arch.

While the implant has been described in the above embodiments of the present disclosure as being a prosthetic heart valve, the disclosure is not limited in this regard. Those skilled in the art can appreciate that in addition to the prosthetic heart valve, the implant delivery system described herein may also be used to deliver other implants to an intended position in the body.

As described above, according to the implant delivery system of the present disclosure, the functional handle can be rotated more conveniently; a more reliable pushing-pulling operation for the functional handle can be obtained, which lowers the risk of operational mistakes; axial and bending performance of the tubular components is greatly improved; the cylindrical boss-like clasps of the stent ear holder allows easier disengagement of the stent frame; the streamlined shape of the tip formed of a flexible polymeric material can reduce the risk of body vascular damage occurring during its delivering, retrieve and retraction; the ability of the functional handle to be operated at two different speeds provides the user more convenience and flexibility; and the braid texture optionally with reinforcing fibers enables the outer tube to have better axial performance with the same wall thickness. Therefore, the implant delivery system of the present disclosure has perceived technical advantages.

Further, according to the present disclosure, in the inner tube assembly, the proximal inner tube and the auxiliary tube form a double-layered structure capable of meeting the requirements for both high axial strength and bending property, compared to a single-layered structure which generally provides a high tensile and compressive strength and hence a high force transfer ability but cannot meet the requirement for a high bending flexibility due to a relatively large tube wall thickness. In the double-layered structure according to the present disclosure, the diametrically smaller proximal inner tube can be made of a metallic or polymeric material to obtain high tensile and compressive resistance capabilities and its smaller diameter ensures a desirable bending property. In addition, the auxiliary tube may be formed of a metallic or polymeric material in a helical shape and can thus provide protection for the proximal inner tube and prevent it from wobbling, and provide a good bending property at the same time.

Further, according to the present disclosure, the implant-loading portion of the distal inner tube that has differing diameters at different sections can ensure that the implant is partially crimped down to a minimal size and that, after the implant is loaded, a portion of it protruding out can well match the inner tube, thus resulting in an improvement of force transfer which in turn facilitates the deployment.

Further, according to the present disclosure, as the diametrically differing sections of the outer tube have different woven structures and different stiffness, they can meet different requirements for strength and bending flexibility. In addition, the woven structures can be further provided with polymeric reinforcing ribs made of polymeric material(s) to obtain improved axial performance.

Further, according to the present disclosure, the stent ear holder made of a metallic or highly radiopaque polymeric material can ensure the visibility of the deployment process and facilitate the operation. In addition, compared to clasps assuming a rectangular or other shape, the cylindrical boss-like clasps for connecting with the implant such as a stent will generate less shear force with the frame of the stent and thus can ensure smooth disengagement of the implant therefrom.

Further, according to the present disclosure, the functional handle can achieve controlled deployment of the implant such as a valve stent at two different models, i.e., precisely deploy by rotating the knob and rapidly deploy by manipulating the button. In addition, the rotating operation and the pushing-pulling operation can be inter-switched arbitrarily at any position as desired.

Further, according to the present disclosure, the arrangement with the fastener, spring and button of the push-pull control member fixed within the casing tube where the threaded rod of the functional handle is disposed in enables a very convenient and easy rotation operation for the user.

Further, according to the present disclosure, as the push-pull member of the delivery system is housed in the cylindrical shell, it can be manipulated in a more reliable and convenient way without causing undesirable effects such as the finger slippery as described above in the Background.

It should be understood that, as used herein, a "proximal end" or a "trailing end" refers to an end adjacent to the user of the deliver system, whilst a "distal end" or a "leading end" refers an end remote from the user of the system.

Although the present disclosure has been described with reference to several specific embodiments, it should be understood that those of ordinary skill in the art can make various modifications and variations without departing from the scope and spirit of the invention. It is therefore intended that the appended claims cover all such modifications and variations that are within the scope of the claimed subject matter.

What is claimed is:

1. An implant delivery system, comprising an inner tube assembly, an outer tube assembly and a functional handle, wherein the inner tube assembly comprises, from a proximal end to a distal end in the sequence set forth, a reinforcing tube, a proximal inner tube, a stent ear holder, a distal inner tube and a tip; the inner tube assembly is configured to allow a guide wire to extend therethrough; the outer tube assembly is disposed over the inner tube assembly and comprises, from a proximal end to a distal end, a proximal outer tube and a stent capsule, the proximal outer tube being received within a stability tube; the functional handle is connected to both the inner tube assembly and the outer tube assembly and the functional handle comprises a threaded rod, a push-pull control member, a casing tube, a displacement tube, an inner tube fixing member, an outer tube fixing member and a stability tube fixing member, the inner tube fixing member being in fixed connection with a proximal portion of the inner tube assembly; the outer tube fixing member being in fixed connection both with a proximal end of the outer tube assembly and with a distal end of the displacement tube, the stability tube fixing member being in fixed connection with a proximal end of the stability tube and fixed to a distal end of the casing tube; the displacement tube is received within the casing tube such that the displacement tube moves forward and backward in the casing tube only along an axis direction of the casing tube; the threaded rod extends through a bore of the displacement tube; the threaded rod defines a leading portion and a trailing portion, the trailing portion of the threaded rod being provided with a knob; the push-pull control member comprises a fastener and a button, the button being provided on the fastener; the displacement tube defines a slot compatible with the fastener, and the fastener is able to extend through the slot to engage a thread of the threaded rod in the displacement tube; the push-pull control member further comprises a cylindrical shell and springs, and the cylindrical shell is disposed over the casing tube such that the button is able to extend out of the cylindrical shell through an opening thereof; the fastener assumes an annular shape and is engageable with the thread provided on the leading portion of the threaded rod; and the springs are disposed between the fastener and the displacement tube and configured to cause an automatic locking of the fastener and the threaded rod, wherein an auxiliary tube fits over a periphery of the proximal inner tube, the auxiliary tube having a distal end abutting a proximal side of the stent ear holder and in fixed connection with both the stent ear holder and the proximal inner tube, the auxiliary tube having a proximal end in connection with both the proximal inner tube and the reinforcing tube.

2. The implant delivery system according to claim 1, wherein the tip is made of a flexible polymeric material and has a leading portion with a streamlined shape and a trailing portion with a straight shape, the trailing portion of the tip having a straight shape portion with a beveled or rounded edge; and/or the tip is radiopaque.

3. The implant delivery system according to claim 1, wherein the distal inner tube is fabricated from a polymeric tube, a coil reinforced polymeric tube or a braid reinforced polymeric tube; and/or the distal inner tube has a stepped profile for loading an implant.

4. The implant delivery system according to claim 1, wherein the stent ear holder is made of a polymeric or metallic material and comprises two or more clasps for connecting an implant, each of the clasps assuming a shape of a cylindrical boss; and/or the stent ear holder has end faces each defining an arc-shaped transition area; and/or the stent ear holder is radiopaque.

5. The implant delivery system according to claim 1, wherein the proximal inner tube is made of a polymeric or metallic material.

6. The implant delivery system according to claim 1, wherein the auxiliary tube is formed of a polymeric material and the auxiliary tube is a polymeric catheter or defines a helical structure at a distal end;

or the auxiliary tube is a metal spring.

7. The implant delivery system according to claim 1, wherein the reinforcing tube is made of a polymeric or metallic material and has one end in connection with both the proximal inner tube and the auxiliary tube; and the reinforcing tube is coupled to the functional handle via the inner tube fixing member, thereby securing the inner tube assembly to the functional handle.

8. The implant delivery system according to claim 1, wherein the outer tube assembly has a tapering shape, with the stent capsule having an outer diameter greater than an outer diameter of the proximal outer tube; and/or both the stent capsule and proximal outer tube are fabricated from a polymeric tube and comprise an outer layer, an intermediate layer and an inner layer, wherein: the outer layer is formed of a high-strength polymeric material; the intermediate layer is a coil layer or a braid layer; and the inner layer is formed of a low-friction polymeric material.

9. The implant delivery system according to claim 1, wherein a section of the proximal outer tube adjacent to the stent capsule is fabricated from a coil reinforced tube or a pure tube and a section of the proximal outer tube remote from the stent capsule is fabricated from a braid reinforced tube; and/or the remote section of the stent capsule is provided with a radiopaque ring.

10. The implant delivery system according to claim 1, wherein the stability tube is fabricated from a coil or braid reinforced polymeric tube or a pure polymeric tube.

11. The implant delivery system according to claim 1, wherein the inner tube fixing member is formed of a high-strength polymeric material or a metallic material, and the reinforcing tube of the inner tube assembly extends through a bore of the inner tube fixing member and is connected to the inner tube fixing member.

12. The implant delivery system according to claim 1, wherein the outer tube fixing member comprises an outer tube fixing base, an outer tube fixing screw cap, an outer tube sealing screw cap and an outer tube sealing ring; the proximal outer tube has an end portion expandable to a flare-shape and can thereby be connected to a distal portion of the outer tube fixing base, the distal portion of the outer tube fixing base having a conical structure matching in shape the flare-shaped end portion of the proximal outer tube; the outer tube fixing screw cap is fastened over the distal portion of the outer tube fixing base such that the flare-shaped end portion of the proximal outer tube is pressed against, and thus in fixed connection with, the outer tube fixing base; the outer tube sealing screw cap is in connection with a proximal end of the outer tube fixing base; and the outer tube sealing ring is disposed between the outer tube sealing screw cap and the proximal end of the outer tube fixing base and is configured to seal a lumen between the outer tube assembly and the inner tube assembly.

13. The implant delivery system according to claim 12, wherein the outer tube fixing base defines an aperture between the flare-shaped end portion of the proximal outer tube and the outer tube sealing ring, the aperture being in connection with an outside of the implant delivery system via an outer tube flush port.

14. The implant delivery system according to claim 1, wherein the stability tube fixing member comprises a stability tube fixing base, a stability tube fixing screw cap, a stability tube sealing screw cap and a stability tube sealing ring; the stability tube has an end portion expandable to a flare shape and can thereby be connected to a distal portion of the stability tube fixing base, the distal portion of the stability tube fixing base having a conical structure matching in shape the flare-shaped end portion of the stability tube; the stability tube fixing screw cap is fastened over the distal portion of the stability tube fixing base such that the flare-shaped end portion of the stability tube is pressed against, and thus in fixed connection with, the stability tube fixing base; the stability tube sealing screw cap is in connection with a proximal end of the stability tube fixing base; and the stability tube sealing ring is disposed between the stability tube sealing screw cap and the proximal end of the stability tube fixing base and is configured to seal a lumen between the stability tube and the proximal outer tube.

15. The implant delivery system according to claim 14, wherein the stability tube fixing base defines an aperture between the flare-shaped end portion of the stability tube and the stability tube sealing ring, the aperture being in connection with an outside of the implant delivery system via a stability tube flush port.

16. The implant delivery system according to claim 1, wherein a Luer lock is in connection with the proximal portion of the inner tube assembly and thus with a lumen of the inner tube assembly.

17. An implant delivery system, comprising an inner tube assembly, an outer tube assembly and a functional handle, wherein the inner tube assembly comprises, from a proximal end to a distal end in the sequence set forth, a reinforcing tube, a proximal inner tube, a stent ear holder, a distal inner tube and a tip; the inner tube assembly is configured to allow a guide wire to extend therethrough; the outer tube assembly is disposed over the inner tube assembly and comprises, from a proximal end to a distal end, a proximal outer tube and a stent capsule, the proximal outer tube being received within a stability tube; the functional handle is connected to both the inner tube assembly and the outer tube assembly and comprises a threaded rod, a push-pull control member, a casing tube, a displacement tube, an inner tube fixing member, an outer tube fixing member and a stability tube fixing member, the inner tube fixing member being in fixed connection with a proximal portion of the inner tube assembly, the outer tube fixing member being in fixed connection with a proximal end of the outer tube assembly and with a distal end of the displacement tube, the stability tube fixing member being in fixed connection with a proximal end of the stability tube and fixed to a distal end of the casing tube; the displacement tube is disposed within the casing tube such that the displacement tube moves forward and backward in the casing tube only along an axis direction of the casing tube; the threaded rod extends through a bore of the displacement tube; the threaded rod is fixed relative to the casing tube in the axis direction of the casing tube and rotatable relative to the casing tube in a circumferential direction of the casing tube; the threaded rod defines a leading portion and a trailing portion, the leading portion defining a thread, the trailing portion being provided with a knob; the push-pull control member comprises a fastener and a button, the button being provided on the fastener; the displacement tube defines a slot compatible with the fastener, and the fastener is able to extend through the slot to engage the thread of the threaded rod in the displacement tube; and a periphery of the threaded rod is provided with a boss received in a recess formed in the casing tube, alternatively, a periphery of the threaded rod defines a recess accommodating a boss provided on the casing tube, wherein an auxiliary tube fits over a periphery of the proximal inner tube, the auxiliary tube having a distal end abutting a proximal side of the stent ear holder and in fixed connection with both the stent ear holder and the proximal inner tube, the auxiliary tube having a proximal end in connection with both the proximal inner tube and the reinforcing tube.

18. The implant delivery system according to claim 17, wherein the inner tube fixing member is disposed inside and fixed to the casing tube.

* * * * *